United States Patent
Chodorge et al.

(10) Patent No.: US 7,868,216 B2
(45) Date of Patent: Jan. 11, 2011

(54) PRODUCTION OF PROPYLENE EMPLOYING DIMERISING ETHYLENE TO 1-BUTENE, HYDROISOMERIZATION TO 2-BUTENE AND METATHESIS BY ETHYLENE

(75) Inventors: Jean-Alain Chodorge, Antony (FR); Christian Dupraz, Rueil Malmaison (FR)

(73) Assignee: IFP Energies Nouvelles, Rueil Malmaison Cedex (FR)

( * ) Notice: Subject to any disclaimer, the term of this patent is extended or adjusted under 35 U.S.C. 154(b) by 1070 days.

(21) Appl. No.: 11/315,096

(22) Filed: Dec. 23, 2005

(65) Prior Publication Data
US 2006/0161033 A1 Jul. 20, 2006

(30) Foreign Application Priority Data
Dec. 27, 2004 (FR) .................................. 04 13964

(51) Int. Cl.
C07C 6/02 (2006.01)
C07C 5/25 (2006.01)
C07C 2/06 (2006.01)

(52) U.S. Cl. ................. 585/324; 585/328; 585/329; 585/330; 585/646; 585/647; 585/650; 585/651; 585/670; 585/511; 585/512

(58) Field of Classification Search ............. 585/324, 585/328, 329, 330, 646, 647, 650, 651, 670, 585/511, 512
See application file for complete search history.

(56) References Cited

U.S. PATENT DOCUMENTS

| | | | |
|---|---|---|---|
| 2,629,753 A * | 2/1953 | Frevel et al. ............. | 585/634 |
| 4,532,370 A * | 7/1985 | Le Quan et al. ........... | 585/512 |
| 5,292,979 A | 3/1994 | Chauvin et al. | |
| 5,502,018 A | 3/1996 | Chauvin et al. | |
| 5,550,304 A * | 8/1996 | Chauvin et al. ........... | 585/512 |
| 6,075,173 A | 6/2000 | Chodorge et al. | |
| 2002/0169346 A1* | 11/2002 | Commereuc et al. ...... | 585/324 |
| 2003/0109766 A1 | 6/2003 | Commereuc et al. | |

FOREIGN PATENT DOCUMENTS

| | | | |
|---|---|---|---|
| EP | 0646413 A | 4/1995 | |
| FR | 2552079 A | 3/1985 | |
| FR | 2669921 A | 6/1992 | |
| FR | 2755130 A | 4/1998 | |
| FR | 2802921 A | 6/2001 | |
| FR | 2804622 A | 8/2001 | |

OTHER PUBLICATIONS

"Petrochemical Processes—Hydrocarbon Processing" Mar. 2003, p. 126.*

* cited by examiner

Primary Examiner—Thuan Dinh Dang
(74) Attorney, Agent, or Firm—Millen, White, Zelano & Branigan, P.C.

(57) ABSTRACT

A process for producing high purity propylene comprises:
a step for dimerizing ethylene to 1-butene;
a step for hydroisomerizing 1-butene to 2-butenes; and
a step for metathesis of 2-butenes by ethylene. Advantageously, the ethylene used to produce the 1-butene and ethylene for metathesis derive from a steam cracking unit. To increase propylene production, the process can use a steam cracking or FCC C4cut as an additional butene source.

27 Claims, 3 Drawing Sheets

PRODUCTION OF PROPYLENE EMPLOYING DIMERISING ETHYLENE TO 1-BUTENE, HYDROISOMERIZATION TO 2-BUTENE AND METATHESIS BY ETHYLENE

The invention relates to a process for producing high purity propylene.

More particularly, it relates to a process employing a step for metathesis of 2-butenes by ethylene in which at least a portion of the 2-butenes is produced by dimerising ethylene.

Propylene is known to be produced by metathesis of 2-butenes with ethylene (ethenolysis). Processes are known in which a C4 cut from steam cracking is treated by hydroisomerizing 1-butene to 2-butenes, followed by deisobutenization, then the effluent is sent for metathesis where it is reacted with ethylene in accordance with the reaction:

$$CH_2—CH=CH—CH_3+CH_2=CH_2 \rightarrow 2CH_2—CH=CH_2$$

Starting from an olefinic C4 cut, that process necessitates selective hydrogenation of butadiene and separating (or transforming) the isobutene.

As an example French patents FR-B-2 755 130 and FR-B-2 802 921 describe the production of propylene by metathesis with ethylene from an olefinic C4 cut (which comprises diolefins, in particular butadiene, 1-butene, 2-butenes, isobutene and acetylenic compounds). The process (which can also produce high purity isobutene) comprises, in succession:
1) selective hydrogenation of diolefins (butadiene) and acetylenic impurities with isomerizing 1-butene to 2-butenes to thermodynamic equilibrium, to produce an effluent containing principally 2-butenes and isobutene, with practically no diolefins or acetylenic compounds;
2) separation by distilling an overhead cut principally containing isobutene and 1-butene (not converted in the first step), and a bottom effluent principally containing 2-butenes and butane, with at most 1% isobutene and at most 1% 1-butene; and
3) metathesis of the 2-butenes from step (2) with ethylene in the presence of a catalyst comprising rhenium oxide on a support, at a temperature of 0° C. to 100° C. and at a pressure equal to the vapour pressure of the reaction mixture at the reaction temperature. Metathesis is followed by propylene separation.

SUMMARY OF THE INVENTION

It has now been discovered that it may be advantageous to form at least part of the 2-butenes for metathesis by dimerising ethylene to 1-butene then by isomerizing (hydroisomerization) the 1-butene to 2-butenes.

Thus, the invention proposes a process for producing high purity propylene characterized in that it comprises in succession:
a) a step for dimerising ethylene to 1-butene;
b) a step for hydroisomerizing 1-butene to 2-butenes; and
c) a step for metathesis of 2-butenes with ethylene.

The following reactions correspond to the three steps of the process (dimerisation, hydroisomerization and metathesis):
a) $2CH_2=CH_2 \rightarrow_{CH2} CH—CH=CH_2$
b) $CH_2—CH=CH—CH_3 \Leftrightarrow CH_2—CH=CH—CH_3$
c) $CH_2—CH=CH—CH_3+CH_2=CH_2 \rightarrow 2CH_2—CH=CH_2$ Thus, ignoring the yields of the units, the balance of the process of the invention is 2 moles of propylene obtained for every 3 moles of ethylene engaged.

In general, the ethylene used to produce 1-butene and ethylene for metathesis derive from a steam cracking unit. It can also derive from a catalytic cracking (FCC) unit.

ADVANTAGES OF THE INVENTION

A first advantage of the process of the invention over processes using a steam cracking or FCC C4 cut is that it is not necessary to carry out intermediate fractionation. Only one stripping step is necessary at the outlet from the hydroisomerization step to eliminate excess hydrogen and, if necessary, $H_2S$ deriving from sulfurizing the hydroisomerization catalyst. In particular, there is no need to eliminate isobutene since in the process of the present invention, the C4 metathesis feed deriving from hydroisomerizing ex-dimerisation 1-butene contains none.

Further, purification on a sieve of the C4 metathesis feed, which is normally necessary for a C4 feed from steam cracking, is no longer necessary in this case.

Finally, a further advantage of the process of the invention when ethylene deriving from a steam cracking unit is used is that the propylene/ethylene ratio at the outlet can be manipulated at will with no limitations as to the availability of the C4 cut, as is the case with conventional metathesis alone.

DETAILED DESCRIPTION OF THE INVENTION

The contents of all documents incorporated by reference into the above description and that which follows should be considered to form an integral part of the description.

The process of the invention is characterized in that it comprises:
a) a step for dimerising ethylene into an effluent essentially constituted by 1-butene;
b) a step for hydroisomerizing 1-butene contained in said effluent to produce an effluent which is rich in 2-butenes; and
c) a step for metathesis with ethylene of 2-butenes from said effluent which is rich in 2-butenes to produce high purity propylene.

Figure 1:
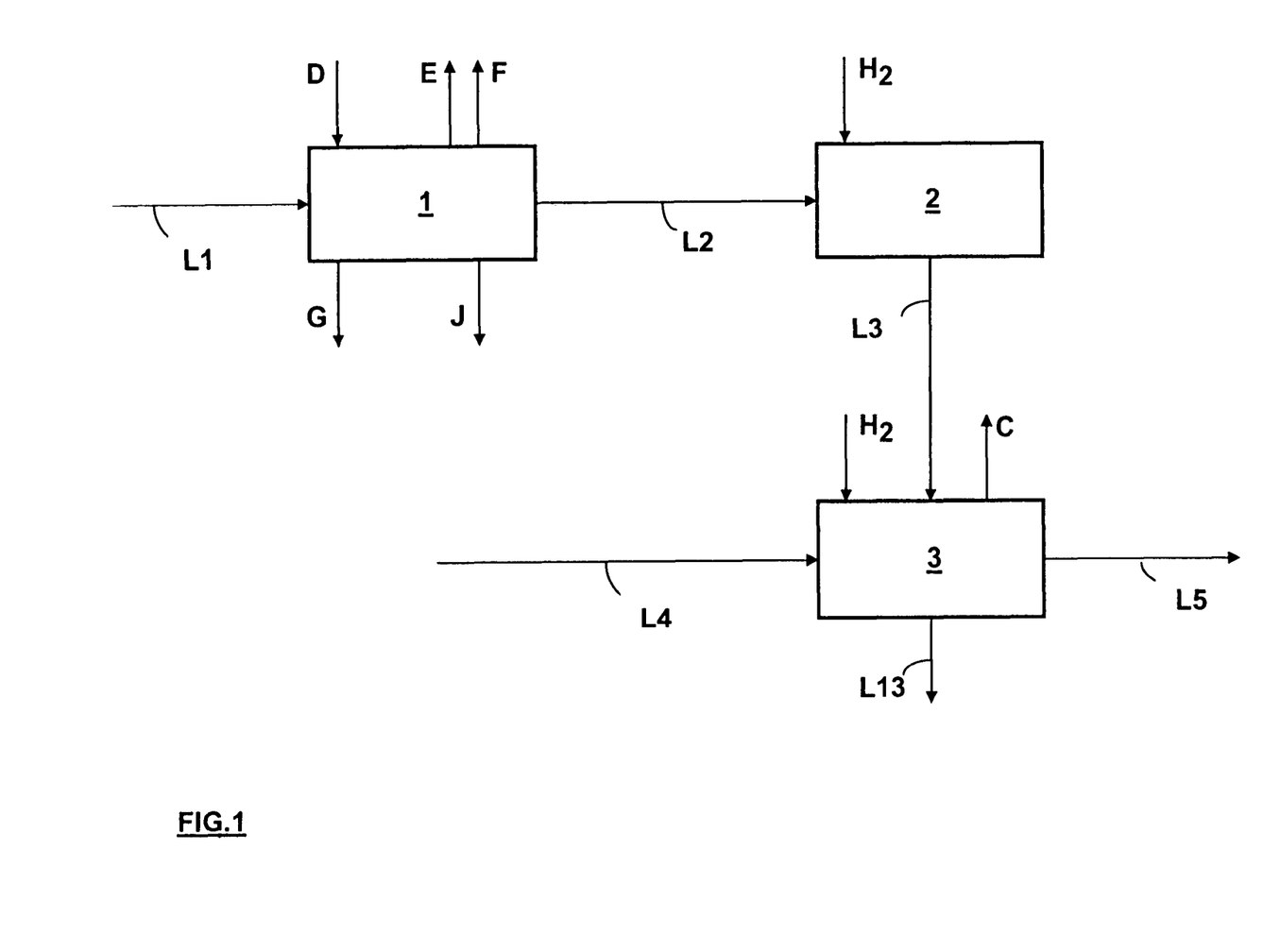
FIG. 1 is a general flow sheet.

The process of the invention will be described below with reference to FIG. 1, which is a general flow sheet.

BRIEF DESCRIPTION OF DRAWINGS

All figures are box flowsheets.

Ethylene arrives via a line L1 at a dimerisation zone 1 in which it is dimerised into butenes, essentially 1-butene. The effluent leaving the dimerisation step via a line L2 is sent to a hydroisomerization zone 2 which receives a stream of hydrogen (H2) and in which the 1-butene is isomerized to 2-butenes. The hydroisomerization effluent, which is rich in 2-butenes, is sent via a line L3 to a metathesis zone 3 which also receives ethylene via a line L4. The effluent from the metathesis zone 3, principally constituted by the propylene produced, leaves via a line L5.

The excess ethylene and unreacted and/or non-reactive C4 compounds are separated; they are recycled in part to the metathesis inlet. The fraction of unreacted and/or non-reactive C4 compounds leaves via a line L13 as a raffinate.

The references C, D, E, F, G and J, which designate certain streams in FIG. 1, will be explained in the example illustrating the invention, presented below in connection with FIG. 2.

Dimerising ethylene to 1-butene

Ethylene can be dimerised by any catalytic process that is known in the art for converting ethylene into light α-olefins. Clearly, preference is given to catalysts that can produce a high dimer selectivity (1-butene).

It is possible to use a certain number of catalytic zirconium oligomerization systems, but they essentially produce mixtures of dimers, trimers and tetramers.

Such catalytic systems have been described in the following documents, for example:

FR-B-2 669 921, which describes the use of a system obtained by pre-reacting a mixture of alkyl zirconate and ether with an aluminium compound;

FR-B-2 689 500, which describes the use of a catalytic zirconium system resulting from reacting an oxo carboxylate zirconium complex with an aluminium compound. The reaction can be carried out in the presence of a ligand such as a carboxylic acid, an ester, an anhydride, an amine, a nitrile or an amide;

FR-B-2 693 455, which more particularly describes a catalytic zirconium system resulting from mixing:

zirconium compound with general formula: $ZrX_xY_yO_z$ (in which X=Cl or Br; Y=—OR, —N(R)$_2$ or —OCOR; R=a hydrocarbyl radical containing 1 to 30 carbon atoms; x and y=0-4; z=0 or 0.5; and x+y+2z=4);

with an organic compound with formula $R_1O$—$CR'_1R'_2$—$OR_2$ (in which $R'_1$ and $R'_2$=H or a hydrocarbyl radical containing 1 to 30 carbon atoms; $R_1$ and $R_2$=a hydrocarbyl radical containing 1 to 30 carbon atoms);

then with a halogenohydrocarbylaluminium with formula $AlR''_nX_{3-n}$ (in which R''=a hydrocarbyl radical containing 1 to 6 carbon atoms; X=Cl or Br; and n=1 or 2);

FR-B-2 748 018, which describes the oligomerizing ethylene using a catalytic zirconium solution obtained by mixing a zirconium compound with an organic compound selected from acetals and ketals, esters, ketones, ethers, amines, nitriles, anhydrides, acid chlorides, amides, aldehydes, thioethers, sulphides and alkyl bisulphides, thiophenes, thioureas and phosphines, and a chlorinated or brominated hydrocarbylaluminium. An additive comprising a quaternary ammonium salt can be added to this catalytic solution to reduce undesirable deposits of solid polymer on the walls of the reactor and the tubes of the heat exchangers.

To increase the activity of such catalytic compositions, as described in FR-B-2 759 922, for example, it is possible to add a tris(hydrocarbyl) aluminium compound with formula $AlR_3$ (in which $R_3$ is a hydrocarbyl radical containing 1 to 6 carbon atoms).

However, to obtain sufficient selectivities for dimers (1-butene), such catalytic systems have to be used at relatively high temperatures and pressures (for example temperatures of the order of 130° C. and pressures of the order of 9 MPa). Even in this case, the butenes have to be separated from hexenes and octenes by fractionation.

Further, in the dimerization step of the process of the invention, it is preferable to use catalytic systems that allow better selectivity for butenes, such as those used in commercial "Alphabutol®" processes.

In a process of that type, the catalyst used may consist of a solution based on alkyl titanate resulting, for example, from the interaction between an alkyl titanate and an aluminium compound with formula $AlR_3$ or $AlR_2H$ in which R represents a hydrocarbyl radical (the aluminium compound is, for example, a trialkylaluminium or hydrogenodialkylaluminium compound).

FR-B-2 552 079 describes a process for synthesizing 1-butene by dimerising ethylene in the presence of a catalyst constituted (a) by a preformed mixture of an alkyl titanate and an ether, in particular in an ether/alkyl titanate mole ratio of 0.5:1 to 10:1, and (b) an aluminium compound with formula $AlR_3$ (trialkylaluminium) or $AlR_2H$ (hydrogenodialkylaluminium). The ether is preferably selected from diethyl ether, diisopropyl ether, dibutyl ether, methyl tertiobutyl ether, tetrahydrofuran, 1,4-dioxan, dihydropyran and ethylene glycol dimethyl ether. Preferably, the catalytic system results from the interaction in a hydrocarbon medium of a trialkylaluminium with a near stoichiometric mixture of an alkyl titanate and tetrahydrofuran. The temperature employed to convert the ethylene to 1-butene is 35° C. to 70° C. (more particularly about 50° C.), the pressure being 1 to 3 MPa, for example.

To improve the purity of 1-butene as described, for example, in FR-B-2 581 381, the crude dimerisation product can be mixed with an amine and distilled at a temperature above the dimerisation temperature to separate better purity 1-butene from the distillation residue containing the catalyst residues. For a dimerisation temperature of 20° C. to 80° C., for example, the distillation temperature may be 90° C. to 180° C. The formula for the amine is $HNR_1R_2$ (in which $R_1$ and $R_2$ are each a hydrogen atom or a hydrocarbon radical and can together form an alkylene group, but are not both a hydrogen atom), for example. The amine preferably contains 5 to 22 carbon atoms.

To reduce undesirable deposits of solid polymer on the walls of the reactor and the tubes of the heat exchanger, an additive consisting a quaternary ammonium salt (as described, for example, in FR-B-2 748 019) or a polyethylene glycol or a polyethylene glycol derivative (as described, for example, in FR-B-2 748 020) can be used.

It is also possible to use a homogeneous catalyst comprising a nickel compound containing a phosphorus-containing ligand such as a phosphine or a phosphite.

It is thus possible to use a homogeneous nickel catalyst comprising a divalent nickel complex containing, for example, two molecules of tertiary phosphine (optionally associated with a divalent nickel compound containing neither water nor phosphine) and an alkylaluminium halide as described, for example, in European patent EP-B-0 646 413. The dimerisation reaction can then be carried out at a pressure of about 5 MPa and at a temperature of about 40° C. The catalyst is optionally employed in an ionic liquid in a non aqueous medium with an ionic nature resulting from bringing at least one aluminium halide or alkylaluminium halide into contact with at least one quaternary ammonium halide and/or at least one quaternary phosphonium halide.

The dimerisation reaction can then be carried out, for example at a pressure of 2 to 9 MPa and at a temperature of −10° C. to +60° C.

It is also possible to use a catalytic composition comprising at least one nickel compound in an ionic medium mixed or complexed with at least one tertiary phosphine carrying a functional group or a phosphite carrying a functional group as described, for example, in FR-A-2 804 622.

The dimerisation catalyst is generally deactivated by an inhibitor. The reaction effluent, free of catalyst, and a concentrated deactivated catalytic solution may be recovered.

To this end, the operation is as follows:
(a) an inhibited catalyst containing the reaction effluent is introduced into a flash column in which the pressure is reduced by 0.1 to 2 MPa, forming a first gas phase containing 1-butene and ethylene and a first liquid phase containing the inhibited catalyst;
(b) the first liquid phase is passed into at least one vaporization zone in which it is vaporized at a pressure that is substantially equal to that of step (a) and at a temperature which can separate a second gas phase containing 1-butene and ethylene and a second liquid phase containing the inhibited catalyst;
(c) the second liquid phase from (b) is passed through at least one thin film evaporation zone and evaporated at a pressure substantially equal to that in step (b) and under conditions that allow separation of a third gas phase containing 1-butene, ethylene and other hydrocarbons and a concentrated deactivated catalytic solution; and
(d) the first, second and third gas phases are recovered to obtain a gaseous reaction effluent which is largely free of catalyst.

That deactivation mode has been described in FR-B-2 733 497, for example.

It is also possible to operate on the ethylene feed in at least two successive steps with catalysts of different types, at least one oligomerization step being carried out in the presence of a catalytic element in a liquid-liquid two-phase medium containing an ionic medium which is not (or is only slightly) miscible with the organic phase. The second step is particularly selective for dimers. The pollutants in the apparatus can be tightly controlled since they are partially eliminated in the first step. Better use of catalyst in the two-phase medium can reduce loss of catalyst. Said operative mode has been described, for example, in FR-A-2 765 573.

Hydroisomerizing 1-butene to 2-butenes

To carry out hydroisomerizing 1-butene to 2-butenes, any process described in the prior art can be employed.

The catalytic composition used in the step for isomerizing 2-butenes can comprise a compound of a transition metal from group VIII, more particularly palladium or nickel.

In particular, the catalysts described in the following documents can be employed.

French patent FR-B-2 355 792 describes the use of a palladium catalyst (containing 0.5% by weight of palladium, for example) on an alumina support, the process comprising a pre-treatment consisting, for example, of bringing it into contact with 2% by weight of water for 2 hours under 25 atmospheres of hydrogen and at an hourly space velocity (HSV) of 40 litres per litre of catalyst per hour.

As described in FR-B-2 718 597, for example, palladium catalysts can be treated in advance with a solution of a sulphur compound then activated in a neutral or reducing atmosphere at a temperature of 20° C. to 300° C. at a pressure of 0.1 to 5 MPa and with an HSV of 50 to 600 h$^{-1}$. The catalyst, containing 0.05% to 10% by weight of sulphur, for example, is then brought into contact with the feed and hydrogen at a temperature of 20° C. to 200° C., at a pressure of 0.1 to 5 MPa and at an HSV of 0.5 to 10 h$^{-1}$ and at an H$_2$/olefin mole ratio of 0.01 to 1.

As described in FR-B-2 735 467, for example, the catalytic composition comprising a compound of a transition metal from group VIII may also contain a quaternary ammonium and/or phosphonium salt (molten salt). The use of a molten salt (quaternary ammonium and/or phosphonium salt) in combination with a transition metal compound, allows the isomerization reaction to be carried out at relatively low temperatures, in a closed, semi-closed or continuous system. The products are easy to separate from the polar catalyst and the latter is recycled in part to the isomerization reactor.

More particularly, with catalysts of that type, the hydroisomerization conditions may, for example, be as follows:
a pressure of 2 to 2.5 MPa;
a temperature of 60° C. to 120° C.; and
an hourly space velocity of 3 to 6 h$^{-1}$ (for example 4 h$^{-1}$).

Metathesis of 2-butenes by ethylene

To carry out metathesis of 2-butenes by ethylene, any process which has been described in the prior art can be employed, in particular a process such as those commercially known as "Meta-4®".

In general, in the metathesis zone, the reagents (ethylene used in excess and the 2-butene feed from the previous step) pass over a bed of catalyst on which the metathesis reaction takes place, this generally being carried out continuously and generally comprising a reaction and a regeneration phase.

Then, for example, a metathesis catalyst can be used which contains rhenium oxide on alumina or on a compound derived from alumina such as a silica-alumina or boron oxide-alumina.

The reaction can then be carried out at a temperature of 0° C. to 100° C., preferably 25° C. to 75° C. It is preferably carried out in the liquid phase and then uses at least one reactor with a moving bed of catalyst, the feed moving from top to bottom or from bottom to top. When operating in the liquid phase, the HSV is preferably in the range 0.1 h$^{-1}$ to 10 h$^{-1}$, at a pressure which is preferably in the range 2 to 8 MPa.

The catalyst can then be employed in a moving bed and passes from a zone in which metathesis reaction conditions prevail and from which it can be withdrawn (for example from the bottom) to be sent to a zone in which regeneration conditions prevail, then returned to the reaction zone (for example to the head thereof).

Regarding regeneration, the catalyst withdrawn from the reaction zone is oxidized outside said regeneration zone with a gas containing 1% to 5% of oxygen at a first temperature, for example 350° C. to 750° C., then with a gas containing 5% to 40% of oxygen at a second temperature, for example 400° C. to 800° C., the second temperature being at least 50° C. above the first. The catalyst is then heated to the metathesis temperature and recycled to the reaction zone for re-use. This has been described in FR-B-2 608 595, for example.

In a further mode in which the metathesis section is employed, the metathesis catalyst can be disposed in a fixed bed in one or more reactors and each reactor is employed in succession in the reaction phase and in the regeneration phase, as described, for example, in FR-B-2 772 022.

According to FR-B-2 726 487 and FR-B-2 726 563, it is also possible to use a catalytic composition containing at least one compound of rhenium and aluminium with general formula:

$$O_3Re-O-(Al(OR)(L)_x-O)_n-ReO_3 \quad (A)$$

in which R represents a hydrocarbyl radical containing 1 to 40 carbon atoms; n is a number from 1 to 10; x is 0 or 1 and L represents the synthesis solvent.

The compositions containing the compound (A) can be used directly in a homogeneous phase, in the solvent resulting from their preparation, in the metathesis reaction. The compound (A) is obtained by contact of Re$_2$O$_7$ with a compound with general formula (RO)$_q$AlR'$_r$, in which R is a hydrocarbon group containing 1 to 40 carbon atoms, R' is a hydrocarbon radical containing 1 to 20 carbon atoms (preferably 1 to 6 carbon atoms); q and r are each one of the values 1 and 2, in which q+r32 3. The compound $(RO)_q AlR'_r$ is readily obtainable from trihydrocarbylaluminium $AlR'_3$ and the alcohol ROH. The compounds (A) are soluble in hydrocarbons, and normally do not require a co-catalyst.

The catalysts can be supported, the support possibly being organic or inorganic as described, for example, in FR-B-2 726 488.

More particularly, as described in FR-B-2 740 056, for example, a catalyst which contains at least one porous inorganic support, from 0.01% to 20% by weight of rhenium in the form of an oxide and 0.01% to 10% by weight of aluminium derived from an aluminium compound with formula $(RO)_q AlR'_r$ in which R is an alkyl group containing 1 to 40 carbon atoms, R' is an alkyl group containing 1 to 20 carbon atoms, q and r are each one of the values 1 and 2 and q+r=3. That catalyst can be prepared by a process which comprises:
- (a) preparing a calcined precursor of the catalyst containing at least one porous inorganic support and rhenium;
- (b) bringing the precursor into contact with a compound with formula $(RO)_q AlR'_r$ obtained by reaction between ROH and $AlR'_3$; and
- (c) drying the resulting product.

It is also possible to use a catalyst containing rhenium, caesium and delta alumina as described, for example, in FR-B-2 784 040. The catalyst contains at least one rhenium compound, for example, deposited on a support principally composed of alumina; it is treated at a temperature of more than 750° C. and modified with at least one caesium compound.

Metathesis catalysts on a porous mineral support containing at least one rhenium, molybdenum or tungsten compound may also comprise silicon as described, for example, in FR-B-2 826 880.

When using a supported catalyst, the support can more particularly consist of an alumina in the form of beads obtained using the "oil-drop" method, for example.

Metathesis is generally carried out in the gas phase at a temperature of 0° C. to 100° C., more particularly at 30° C. to 60° C. and still more particularly at a temperature of about 35° C.

As an example, the pressure can be 2 to 6 MPa, more particularly about 4.5 MPa. The mass flow rate with respect to the mass of catalyst of the combined feeds (butenes and ethylene) at the reactor inlet can, for example, be 1 to 2 $h^{-1}$, more particularly about 1.5 $h^{-1}$.

Normally, the metathesis zone also comprises a de-ethenizer to separate excess ethylene which is recycled at least in part to the metathesis zone, and a propylene separation column which can separate the high purity propylene which is produced, and unreacted butenes. They are recycled in part to the metathesis reactor.

Advantageously, in the process of the invention, the ethylene used to produce 1-butene and ethylene for metathesis derives from a steam cracking unit.

In the process of the invention, in addition to the 2-butenes obtained by dimerising ethylene to 1-butene, then isomerizing 1-butene to 2-butenes, it is also possible to use a C4 steam cracking cut or C4 catalytic cracking cut (FCC) as an accessory source of butenes.

If it is a C4 steam cracking cut, as is known, it can be treated in succession by:
- hydroisomerizing said cut to 2-butenes and isobutene;
- eliminating isobutene (de-isobutenization);
- purification on a sieve; and
- sending to the metathesis inlet.

The C4 cut principally contains isobutene, butenes (essentially 1-butene) and butadiene.

Figure 2:
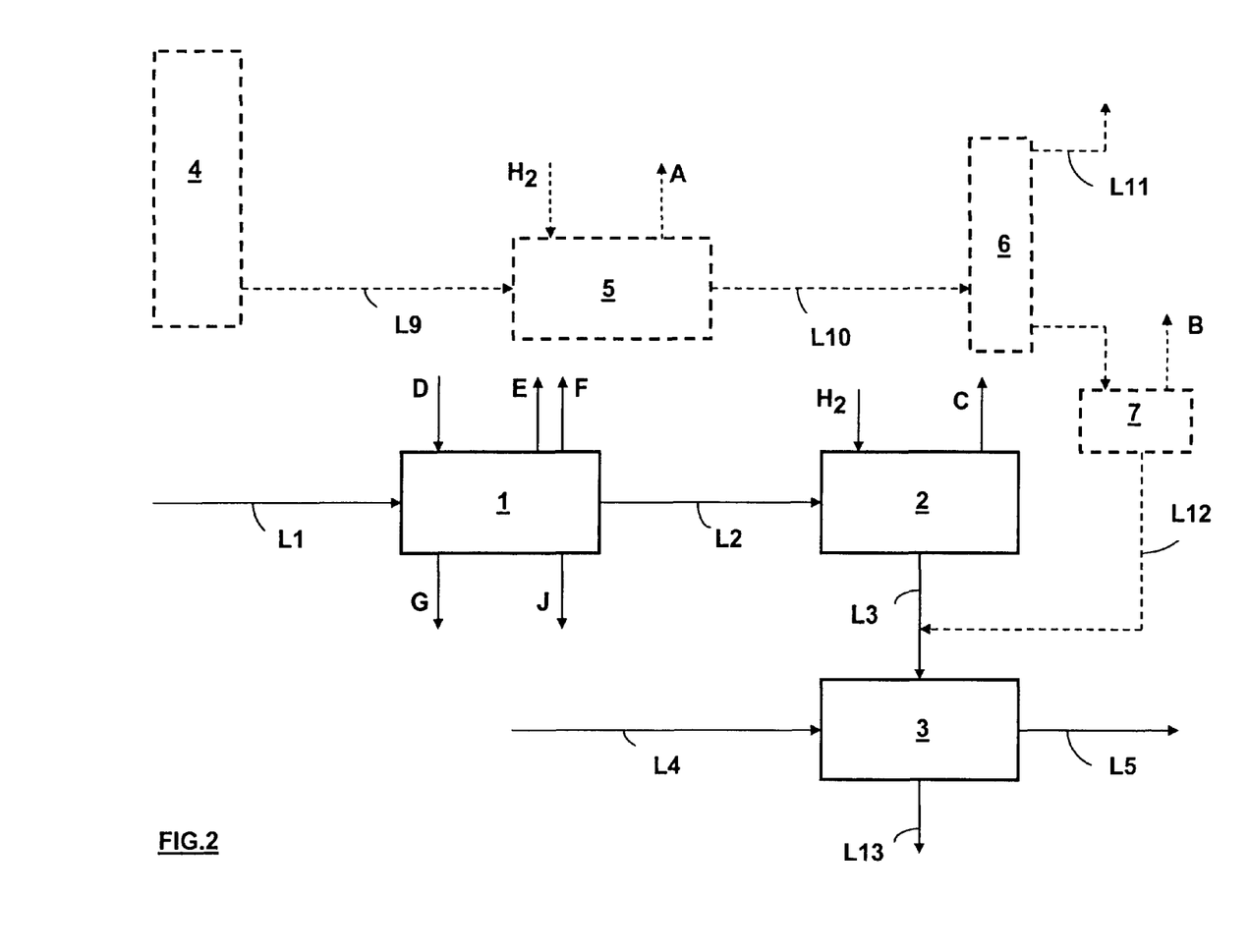
FIG. 2 is a flowsheet for the EXAMPLE hereinafter described, wherein box 4 is a steam cracker which provides a cut of butene-1.

Such a variation in the process of the invention is shown as a dotted line in the accompanying FIG. 2. The C4 cut from the steam cracking zone 4 is sent via a line L9 to the zone for selective hydrotreatment of butadiene, followed by hydroisomerization (zone 5), in which the butadiene is selectively hydrogenated to butenes, then the 1-butene is transformed into 2-butenes. The effluent leaving via the line L10 principally contains 2-butenes and isobutene. That effluent is sent to a separation zone 6 in which, for example by distillation, an overhead effluent principally constituted by isobutene is separated via a line L11 and a bottoms effluent principally constituted by 2-butenes is separated via a line L12. Said effluent is combined with the effluent leaving the hydroisomerization zone 2 via a line L3 to supply the metathesis zone 3.

Hydroisomerization

Hydroisomerizing 1-butene to 2-butenes can be carried out using techniques described in the prior art.

Regarding the isomerizing external olefins (1-butene) to more strongly substituted olefins and/or to internal olefins (2-butenes) in a feed containing a diolefin (1,3-butadiene), as described in FR-B-2 708 596, it is possible to pre-treat the catalyst with a solution of a sulphur compound then activate by treatment in a neutral or reducing atmosphere at a temperature of 20° C. to 300° C. at a pressure of 0.1 to 5 MPa and at an HSV of 50 to 600 $h^{-1}$. The catalyst containing, for example, 0.05% to 10% by weight of sulphur, is then brought into contact with the feed and hydrogen at a temperature of 20° C. to 200° C. at a pressure of 0.1 to 5 MPa at an hourly space velocity of 0.5 to 10 $h^{-1}$ and a $H_2$/diolefin mole ratio of 0.5 to 5.

As described in FR-B-2 752 236, for example, it is possible to treat the feed in a first hydroisomerization reaction zone, Ri1, and the effluent is treated in a distillation zone associated with a second hydroisomerization reaction zone Ri2. The liquid feed for zone Ri2 is removed from the distillation column and the effluent from Ri2 is reintroduced in part into the column at a similar level, to ensure continuous distillation and finally produce an overhead effluent which is rich in isobutene and is of high purity and a bottoms effluent which is rich in 2-butenes. Zone Ri2 is at least partially external to the distillation zone.

When carrying out said operation, hydroisomerizing 1-butene to 2-butenes is carried out as well as selective hydrogenation of diene compounds such as butadiene, vinylacetylene and methyl and ethyl acetylenes.

Elimination of Isobutene (de-isobutenization)

After hydroisomerization, the butenes are separated, for example by distilling the isomerization effluent, to obtain an overhead cut principally containing isobutane (especially in the case of using a C4 FCC cut), as well as isobutene and 1-butene (respectively non-reactive or unconverted in the hydroisomerization step) and a bottom effluent principally containing 2-butenes and n-butane with at most 1% isobutene, for example.

The butenes can be fractionated in a column which, for example, functions at a pressure of 0.4 to 1.2 MPa, with a reflux ratio of 6/1 to 15/1 with respect to the liquid distillate.

The isobutene content can also be reduced by etherification using a mono alcohol such as methanol (thus forming MTBE) and/or ethanol (thus forming ETBE).

Purification

The bottoms effluent can be purified by adsorption onto various adsorbents, for example molecular sieves (for example of the 3A, 4A or 13X type) or on activated alumina.

Figure 3:
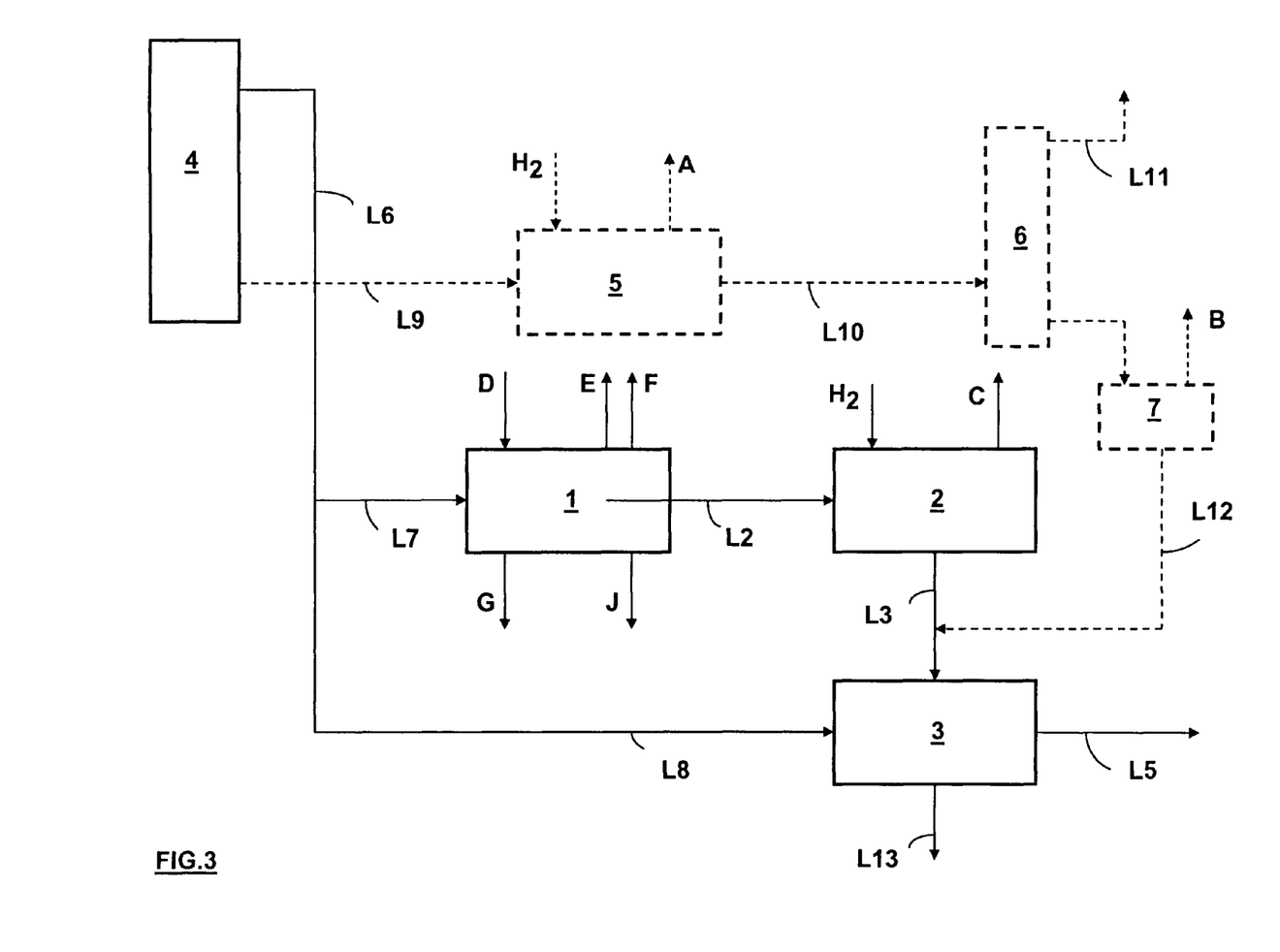
FIG. 3 is a flowsheet wherein box 4 is a steam cracker which also provides an ethylene cut.

Advantageously, in the process of the invention, the ethylene used to produce 1-butene and ethylene for metathesis derives from a steam cracking unit. FIG. 3 diagrammatically shows this implementation.

In steam cracking zone 4, ethylene leaves via line L6. A fraction of said stream is removed and sent via a line L7 to the dimerization zone 1, in which ethylene is principally dimerised to 1-butene. The effluent principally constituted by 1-butene is sent via line L2 to a hydroisomerization zone 2 in which the 1-butene is transformed into 2-butenes. The effluent, principally constituted by 2-butenes, leaves via line L3. This effluent is sent to a metathesis zone 3.

A further ethylene fraction from the steam cracking zone 4 is sent via a line L8 to the metathesis zone 3 to react with the 2-butenes. The effluent from the metathesis zone 3, principally constituted by propylene product, leaves via line L5.

The ethylene employed to produce the 1-butene and ethylene for metathesis can also derive from a catalytic cracking unit.

EXAMPLE

The following example illustrates the invention.

This example describes an implementing the process of the invention with reference to FIG. 2, in which:

C4s for metathesis derive in part from dimerising ethylene and in part from a C4 steam cracking cut; and the same polymer quality ethylene is used for dimerisation and for metathesis.

In the tables presented in this example, the references in parentheses refer to the corresponding streams in FIG. 2.

A C4 cut from steam cracking 4 and with the composition shown below was supplied at a flow rate of 250000 tonnes/year to a pre-treatment section which included a selective hydrotreatment unit (in a hydroisomerization zone 5), a butene fractionation unit with separation of isobutene (in a zone 6) and a molecular sieve purification unit (in a zone 7).

| Composition | Wt |
|---|---|
| C3 | 0.4 |
| Butadienes + acetylenes | 45.0 |
| Isobutene | 12.0 |
| 1-butene | 11.0 |
| Cis 2-butene | 3.0 |
| Trans 2-butene | 4.0 |
| n-butane | 20.0 |
| Isobutane | 4.0 |
| C5 | 0.6 |
| Total | 100.00 |

The hydroisomerization conditions (in zone 5) were as follows:

hydrogen pressure 2.3 MPa and temperature 80° C.;

catalyst: palladium on alumina, pre-sulphurized.

In zone 6, butene fractionation was carried out in a column operating at a pressure of 1 MPa with a reflux ratio of 10/1 with respect to the liquid distillate.

In zone 7, purification was carried out in an adsorption unit on molecular sieve.

The stream flow rates at the inlet and outlet for the pre-treatment section were as follows:

| Inlet (tonnes/yr) | | Outlet (tonnes/yr) | |
|---|---|---|---|
| C4 feed (L9) | 250000 | Feed for metathesis (L12) | 197715 |
| Hydrogen gas (H2) | 6248 | Isobutene-rich cut[1] (L11) | 55000 |
| | | Purges to fuel gas (A) + (B) | 3533 |
| Total | 256248 | Total | 25648 |

| Composition | Wt, % |
|---|---|
| Propane + propylene | 1.6 |
| Isobutane | 18.0 |
| n-butane | 10.7 |
| Isobutene | 48.8 |
| 1-butene | 17.0 |
| 2-butenes | 3.9 |
| Total | 100.00 |

[1]Estimated composition (weight %)

Further, a section comprising a dimerisation unit 1 and a hydroisomerization unit 2 was supplied with ethylene. The ethylene feed had the following characteristics:

purity: at least 99.95 mole % impurities (methane+ethane): at most 500 ppm by volume.

The dimerisation conditions included a (relative) ethylene pressure of 2.3 MPa and a temperature of 50° C. The dimerisation catalyst was constituted by a preformed mixture of an alkyl titanate and an ether and an aluminium compound.

The hydroisomerization conditions included a (relative) hydrogen pressure of 2.3 MPa and a temperature of 80° C. The catalyst was a palladium on alumina, presulphurized catalyst.

The flow rates for the streams at the inlet and outlet for this section were as follows:

| Inlet (tonnes/yr) | | Outlet (tonnes/yr) | |
|---|---|---|---|
| Ethylene feed (L1) | 242726 | n-butene product[1] (L3) | 220000 |
| Catalyst + (D) chemical products | 1474 | C6+ by-products[2] (J) | 18326 |
| Hydrogen gas (H2) | 112 | Ethylene purge[3] (F) | 4114 |
| | | Purges to flare (C + E) | 1278 |
| | | Lost catalyst (G) (to incinerator) | 594 |
| Total | 244312 | Total | 244312 |

| Composition | Wt, % |
|---|---|
| C4 | 0.6 |
| Hexenes | 90.6 |
| | (principally 2-ethyl-1-butene) |
| Hexane | 6.3 |
| Octenes | 2.5 |
| Total | 100.00 |

-continued

| Composition | % wt |
|---|---|
| Methane | 1.7 |
| Ethane | 1.4 |
| Ethylene | 68.6 |
| 1-butene | 28.3 |
| Total | 100.00 |

It was recycled to the steam cracker.

[1] the n-butenes product had a 2-butenes/1-butene ratio of 12/1;
[2] the C6+ stream had the following composition:
[3] The ethylene purge and dimerisation consisted of deconcentration deriving from the recycle column purging light inert compounds such as nitrogen and methane to prevent the pressure in the unit from rising. Its estimated composition was as follows:

The Metathesis Section

The metathesis section 3 was supplied with the mixture of C4 cuts derived on the one hand from the section for pre-treating the C4 steam cracking cut arriving via line L12 and on the other hand from the ethylene dimerisation-hydroisomerization section arriving via line L3.

The metathesis conditions were as follows:

the catalyst was based on rhenium oxide;

the temperature was 35° C. and the pressure was 4.5 MPa.

At the outlet from the metathesis unit 3, the stream leaving via line L5 passed into a de-ethenizer (not shown in FIG. 2), the ethylene leaving overhead was separated into an ethylene purge and an ethylene reactor recycle. Unreacted C4s leaving via line L13 were recycled in part to the reactor and purged in part (C4 raffinate). The recycles are not shown in FIG. 2.

The global material balance for the metathesis unit was as follows:

| Inlet (tonnes/yr) | | Outlet (tonnes/yr) | |
|---|---|---|---|
| C4 feed from pre-treatment[1] (L12) | 197715 | Propylene product (L5) | 475000 |
| C4 feed from dimerisation + hydroisomerization[1] (L3) | 220000 | C4 raffinate[2] (L13) | 99285 |
| Ethylene makeup (L4) | 164432 | Purge[3] | 5462 |
| | | Losses | 2400 |
| Total | 582147 | Total | 582147 |

| Composition | Wt, % |
|---|---|
| C3 | — |
| Isobutane | — |
| Isobutene | 0.9 |
| n-butane | 12.2 |
| 1-butene | 4.4 |
| 2-butenes (cis + trans) | 82.3 |
| C5 | 0.4 |
| Total | 100.0 |

| Composition | % wt |
|---|---|
| C3 | 0.2 |
| Isobutane | — |
| n-butane | 49.9 |
| Isobutene | 1.1 |
| 1-butene | 7.9 |
| 2-butenes, cis + trans | 20.9 |
| C5+ | 20.0 |
| Total | 100.0 |
| Methane | 0.4 |
| Ethane | 2.1 |
| Ethylene | 94.8 |
| Propylene | 2.7 |
| Total | 100.00 |

[1] The mixture of C4 feeds, at a global flow rate of 417715 tonnes/year, had the following composition:
[2] Unreacted C4s leaving the metathesis unit after separating the propylene product had the following composition:
[3] The liquid C2 purge from the head of the de-ethenizer (not shown in FIG. 2) had the following composition:

The invention claimed is:

1. A process for producing high purity propylene, comprising:
    a) dimerising ethylene into an effluent consisting essentially of 1-butene;
    passing said effluent and hydrogen directly into a hydroisomerization reactor, containing a hydroisomerizing catalyst, and
    b) catalytically hydroisomerizing 1-butene contained in said effluent to produce an effluent rich in 2-butenes and having no isobutene, and
    c) in a metathesis reactor containing a metathesis catalyst, said metathesis reactor being separate from said hydroisomerization reactor, conducting metathesis with ethylene of 2-butenes in said effluent rich in 2-butenes to produce high purity propylene, whereas said hydroisomerizing catalyst comprises a group VIII metal and the metathesis catalyst comprises at least one rhenium, molybdenum or tungsten compound, and wherein said metathesis is conducted at a lower temperature than said hydroisomerizing of 1-butene.

2. A process according to claim 1, wherein (a) dimerising ethylene to 1-butene, is conducted in contact with a catalytic system is employed which results from the interaction between an alkyl titanate and an aluminium compound with one of formulae AlR$_3$ and AlR$_2$H in which R represents a hydrocarbyl radical.

3. A process according to claim 2, wherein the catalytic system is (i) a preformed mixture of an alkyl titanate and an ether in an ether/alkyl titanate mole ratio of 0.5:1 to 10:1, and (ii) said aluminium compound.

4. A process according to claim 3, wherein the catalytic system results from the interaction, in a hydrocarbon medium, of a trialkylaluminium with a substantially stoichiometric mixture of an alkyltitanate and tetrahydrofuran.

5. A process according to claim 1, wherein step (a) for dimerising ethylene to 1-butene is conducted in contact with a catalytic system comprising a nickel complex.

6. A process according to claim 5, wherein the nickel complex contains at least one phosphorus-containing ligand.

7. A process according to claim 5, wherein said catalytic system comprises a nickel complex in a non-aqueous ionic liquid.

8. A process according to claim 1 wherein (b) hydroisomerizing 1-butene to 2-butenes is conducted in contact with a catalytic system comprising palladium on a support.

9. A process according to claim 8, wherein the catalyst is pre-sulphurized.

10. A process according to claim 1 wherein (c) metathesis of 2-butenes using ethylene is conducted in contact with a catalytic system which comprises at least one rhenium compound.

11. A process according to claim 1 wherein metathesis comprises a de-ethenizer to separate excess ethylene which is recycled to the metathesis reactor, and a propylene separation column for separating the propylene and unreacted butenes the latter being recycled in part to the metathesis reactor.

12. A process according to claim 1 further comprising:
   d) transforming a C4 steam cracking cut or catalytic cracking cut by hydroisomerization;
   e) de-isobutenizing the stream from d);
   f) purifying the stream from (e) by adsorption; and
   g) sending the stream from (e) to the metathesis (c), along with the stream of 2-butenes from the hydroisomerization (b).

13. A process according to claim 12, wherein the de-isobutenisation of (e) is carried out by distillation.

14. A process according to claim 12, wherein de-isobutenizing (e) is carried out by etherification with methanol or ethanol.

15. A process according to claim 1 further comprising conducting steam cracking to produce the ethylene used to produce 1-butene.

16. A process according to claim 1 further comprising conducting steam cracking to produce the ethylene used for metathesis.

17. A process according to claim 1, wherein the ethylene used to produce 1-butene derives from a catalytic cracking unit.

18. A process according to claim 17, wherein the ethylene used for metathesis derives from a catalytic cracking unit.

19. A process according to claim 1 further comprising polymerizing the produced propylene.

20. A process according to claim 12, wherein the ethylene for (a) is a steam cracking cut or catalytic cracking cut.

21. A process according to claim 1, wherein the hydroisomerization effluent rich in 2-butenes has a ratio of 2-butene to 1-butene of at least about 12:1.

22. A process according to claim 1, wherein the hydroisomerization effluent rich in 2-butenes has a ratio of 2-butene to 1-butene of about 12:1.

23. A process according to claim 1, wherein the metathesis reaction is conducted at a temperature lower than 100° C.

24. A process according to claim 1, wherein the hydroisomerization reaction is conducted at a pressure of 2 to 2.5 MPa, a temperature of 60-120° C. and an hourly space velocity of 3 to $6h^{-1}$.

25. A process according to claim 1, wherein the metathesis reaction is conducted at a pressure of 2 to 8 MPa, a temperature of 25-75° C. and an hourly space velocity of 0.1 to $10h^{-1}$.

26. A process according to claim 24, wherein the metathesis reaction is conducted at a pressure of 2 to 8 MPA, a temperature of 25-75° C. and an hourly space velocity of 0.1 to $10h^{-1}$.

27. A process according to claim 26, wherein the hydroisomerization effluent rich in 2-butenes has a ratio of 2-butene to 1-butene of at least about 12:1.

* * * * *